United States Patent [19]

Muller

[11] 4,160,763

[45] Jul. 10, 1979

[54] IMMUNOGLOBULIN HAVING A REDUCED COMPLEMENT FIXATION, A PROCESS FOR ITS PREPARATION AND AGENTS CONTAINING THIS IMMUNOGLOBULIN

[75] Inventor: Hans Müller, Dautphetal-Buchneau, Fed. Rep. of Germany

[73] Assignee: Behringwerke Aktiengesellschaft, Marburg, Fed. Rep. of Germany

[21] Appl. No.: 862,668

[22] Filed: Dec. 21, 1977

[30] Foreign Application Priority Data

Dec. 23, 1976 [DE] Fed. Rep. of Germany ....... 2658334

[51] Int. Cl.$^2$ .................. A23J 1/06; A61K 37/04
[52] U.S. Cl. .................. 260/112 B; 424/101
[58] Field of Search .................. 260/112 B; 424/101

[56] References Cited

U.S. PATENT DOCUMENTS

| 4,059,571 | 11/1977 | Tomibe et al. | 260/112 B |
| 4,075,193 | 2/1978 | Campbell et al. | 260/112 B |

Primary Examiner—Walter C. Danison
Attorney, Agent, or Firm—Curtis, Morris & Safford

[57] ABSTRACT

The invention relates to immunoglobulin preparations having a reduced complement fixation, a process for their production by treating an immunoglobulin fraction with a low concentration of a sulfitolytic agent and/or phosphate which is sparingly soluble in water and medicaments which contain the immunoglobulin preparations, in particular preparations for intravenous administration.

17 Claims, No Drawings

IMMUNOGLOBULIN HAVING A REDUCED COMPLEMENT FIXATION, A PROCESS FOR ITS PREPARATION AND AGENTS CONTAINING THIS IMMUNOGLOBULIN

The invention relates to immunoglobulin preparations having a reduced complement fixation, a process for their production and medicaments which contain the immunoglobulin preparations, in particular preparations for intravenous administration.

By virtue of their antibody properties, the immunoglobulin preparations which have been produced by fractionation of serum, in particular starting from human serum, are of considerable importance as prophylactic and therapeutic agents for assisting endogenous defensive reactions.

Immunoglobulin preparations have hitherto proved themselves suitable essentially only for intramuscular use; when administered intravenously, the recipients have shown a more or less marked reaction of the anaphylactoid type. It is, however, very desirable to administer the immunoglobulin preparations intravenously, since their effect manifests itself more rapidly in the organism.

It is assumed that the anaphylactoid side-reactions depend on the fixation of the serum complement, caused by the immunoglobulin administered. Attempts have, therefore, frequently been made in the past to modify the immunoglobulins in such a way that their antibody activity is retained, but the extent of the complement fixation is reduced so far that the modified immunoglobulins can be employed for intravenous administration. It is known to modify immunoglobulins by enzymatic degradation so that the fixation points for the complement are split off, but the remainder of the molecules still remain capable of binding the antigens. A preparation of this type has been administered intraveneously with good results.

In some cases the immunoglobulin, the molecule of which has been made smaller, is regarded, because of its comparatively shortened half-life in the organism, as less satisfactory than immonoglobulin preparations in which the molecular weight is substantially unaltered.

The reaction of immunoglobulins with alkylating and acylating agents, in order to prepare immunoglobulins which can be administered intraveneously, has also been described.

Processes are also known in which immunoglobulins are split by reducing the intramolecular disulfide bonds and the sulfhydryl groups formed are subsequently alkylated.

Attempts have also already been made to split the disulfide bonds in the immunoglobulin molecule by sulfitolysis, for which relatively high concentrations of sulfite or tetrathionate are employed. The use of sulfite together with Cu-II ions led to products which received a poor assessment.

The present invention is based on the idea that the main part of intolerance reactions when commercially available gamma-globulins are administered intravenously is not brought about by the gamma-globulin molecule itself but by structures which differ from the natural state of the immunoglobulins.

The invention accordingly relates to immunoglobulin preparations and to a process for their production in which, by means of sulfitolytic measures, the formation of complement-fixing structures prevented or structures already present are modified or removed by adsorption to such an extent that they have only a slight capability, or none at all, for fixing the complement.

The immunoglobulin preparations according to the invention are obtained by a process wherein an immunoglobulin fraction which can be obtained by known processes of fractionating blood plasma is treated with a low concentration of a sulfitolytic agent and/or a quantity, sufficient to reduce the fixation of complement, of a phosphate which is sparingly soluble in water.

For the purposes of the invention, a low concentration of a sulfitolytic agent represents a concentration of $>0$ but $<5\times10^{-2}$ M/l, preferably $2-4\times10^{-3}$ M/l.

The sulfitolytic agent used is generally a sulfite. In accordance with the invention, however, a bisulfite, such as sodium metabisulfite, is preferred, and is advantageously employed in a concentration of 1.3 to $3.6\times10^{-3}$ M/l. Oxidizing substances, such as dithionite and heavy metal ions, such as $Cu^{2+}$ ions, can be used together with the sulfite. They can be employed, in accordance with the invention, within the range from $>0$ but $<5\times10^{-3}$ M/l; as a rule 1/10 of the quantity of the sulfitolytic agent, relative to the molarity. The temperature at which the sulfitolytic substance is added to the immunoglobulin solution is not critical, provided that the temperatures are not substantially higher than 50° C. The process is preferably carried out at a temperature between $+5°$ C. and 25° C. In spite of this general statement, it should be noted that the temperatures exert an influence on the process to the extent that lower concentrations of the reducing agent are required at higher temperatures.

The reaction time is also inversely proportional to the concentration of the sulfitolytic agents. The sulfitolysis of the immunoglobulin fraction is generally carried out for 5–90 hours.

The reaction is terminated by separating the sulfitolytic agents from the immunoglobulins. For this purpose it is appropriate to precipitate the immunoglobulins. Another possibility consists, for example, in removing the sulfitolytic agents by dialysis.

It has proved appropriate not to leave out the treatment of immunoglobulin preparations which can be obtained in accordance with the state of the art, until a last reaction stage. On the contrary, it is more advantageous when the last purification stages, such as are generally customary for the immunoglobulin preparation, follow the process according to the invention.

The starting material for the process according to the invention is an immunoglobulin which can be obtained in accordance with the start of the art. This substance is also designated in several places in the literature as gamma-globulin, IgG and immunoglobulin G. It consists mainly of the so-called 7 S fraction having a molecular weight of about 160,000. Both the immunoglobulins which can be obtained from mixed sera and those which can be obtained from specially immunized donors can be employed in accordance with the invention. These are the so-called hyperimmunoglobulins which have higher than average antibody contents specifically directed against certain antigens. Mumps immunoglobulin should be mentioned here as an example. The starting materials which are suitable for the process according to the invention can be obtained from blood plasma by customary processes, such as, for example, by fractional salt precipitation of plasma or by precipitation with organic solvents, in particular by ethanol, using the various process variants which go back to the fundamental researches of Cohn et al., J. Am. Chem. Soc. 68, (1946), page 449 et seq.

A starting material which is preferentially suitable is a γ-globulin-containing fraction which is called fraction II and III by Cohn or fraction A by Nitschmann. Besides γ-globulin, fractions of this type also contain α-globulin and β-globulin as well as small quantities of albumin. The γ-globulin content is about 40–80% by weight, relative to the quantity of total protein.

It has proved appropriate to dissolve, in water or in a low-concentration, preferably about 0.3–0.9% strength, solution of a neutral salt, such as sodium chloride, a gamma-globulin fraction which is produced in the course of the alcohol fractionation process and has not yet been purified, mostly the paste produced during the fractionation of albumin. After being dissolved, the protein should appropriately be present in a concentration of 0.5 to 15%, preferably between 1 and 5% (g/v). The sulfitolytic agent (for example $Na_2S_2O_5$ or $Na_2SO_3$) and, if desired, a heavy metal salt (for example $CuSO_4$) is added to this solution at a pH value between 4 and 8, preferably at pH 5.0 to 6.0, and a temperature between 5° and 50° C. is maintained.

The pH value of the reaction mixture can deviate during the reaction from its initial value without disadvantageous consequences being produced thereby. After the reaction with the sulfolytic agents, the further purification of the immunoglobulin can be continued directly in the customary manner.

It has, above all, proved suitable to incorporate into the process stages of further purification, an adsorption on a phosphate which is sparingly soluble in water, since end products of the immunoglobulin purification process which have been treated in this way exhibit a reduced complement fixation.

Thus, for example, aluminum phosphate can be prepared in situ in the solution from $AlCl_3$ and $Na_3PO_4$. Besides impurities, complement-fixing aggregates of the immunoglobulin can thereby also become bound to the aluminum phosphate. Calcium phosphate can also be employed for removing impurities and complement-fixing substances.

5–90 hours after the sulfitolytic agents have been added, the immonoglobulins can be precipitated in a manner which is in itself known, for example with ethanol. Purification can also be carried out via ion exchangers. The immunoglobulins are obtained in a particularly pure state if cation exchangers are employed at a weakly acid pH value. A residual content of Cu can be removed by means of compounds, also in the form of ion exchangers, which form metal chelates.

By virtue of the partial sulfitolysis which has been carried out, the immunoglobulin preparations which can be obtained in this way are, in respect of complement-fixing capacity, less strongly complement-fixing than the starting material. This effect can, if desired, be further diminished by the adsorption of complement-binding activity.

Independently of purification results which may be desired at the same time, particularly good results are achieved in respect of the reduced complement-fixation, if immunoglobulin fractions are treated with a phosphate which is sparingly soluble in water. It is preferable to employ aluminum phosphate or calcium phosphate for this purpose.

Quantities of 0.005 to 0.1 M/l are advantageous for this purpose. The adsorbents are appropriately prepared in the immunoglobulin solution itself by adding a water-soluble cation and a water-soluble phosphate which are known to be capable of forming sparingly soluble phosphates with one another. It is appropriate for this purpose to keep the pH value between 4 and 8.5, pH values between 4 and 6 being preferred for the adsorption of complement-fixing activity with the aid of $AlPO_4$ and pH values between 5.8 and 8.5 being preferred for alkaline earth metal phosphates, such as calcium phosphate. Customary water-soluble cations which are capable of forming sparingly soluble precipitates with phosphate ions are aluminum, preferably in the form of $AlCl_3$ or $(Al)_2(SO_4)_3$, and also, amongst the water-soluble alkaline earth metal salts, especially water-soluble calcium salts, such as calcium acetate. It is appropriate to use a slight excess of the cationic component for the formation of the adsorbent in the immunoglobulin solution.

If the sulfitolysis is now combined with an adsorption stage as defined in the preceding statements, it is possible to reduce the complement-fixation of the immunoglobulin preparations to particularly low values, frequently near to 0. Each stage is, however, suitable in itself for reducing the complement-fixation of the immunoglobulin preparations.

Since the object of the process consists in reducing the complement-fixation, the process stages are as far as possible matched with one another in such a way that the products which can be obtained by the process according to the invention meet this requirement.

It accords with the inventive concept if the process is carried out under conditions which the expert recognizes as particularly suitable in this respect. That is to say, that a combination of high concentrations of the sulfitolytic agents in relation to a low protein concentration, a low temperature and a brief reaction time should be co-ordinated within the limits described, and conversely.

The determination of the anticomplementary action is carried out in a hemolysis test using sensitized wether erythrocytes and guinea-pig serum (complement). In this test, the erythrocytes and the complement are reacted with the immunoglobulin preparation. After a suitable incubation time it can be seen that, even at high concentrations, the immunoglobulin preparation hardly interferes at all with the hemolysis, which can be determined quantitatively by photometric means. Furthermore, it can be demonstrated in an in vivo test on rabbits, that no inactivation of the complement factor C1 can be detected after the immunoglobulin preparation according to the invention has been administered intravenously.

In a series of preparations carried out in accordance with the invention, all the complement-fixations are below 10%, relative to a 100% standard. This value is only displaced insignificantly in an upward direction even after storing a preparation for about two years. The proportions of aggregate in the immunoglobulin preparations are also below 10%. When using $CuSO_4$, the order of magnitude in which copper-II ions can be detected is $<1$ μg/ml in a 5% strength protein solution.

The new gamma-globulin preparation with reduced anti-complement activity contains 7 S immunoglobulin which is essentially unchanged when compared with the modified preparations of the state of the art, some of which have lower sedimentation values. The antibody activity of the molecule is retained.

The immunoglobulin preparations which can be produced in accordance with the invention are primarily intended for intravenous administration. A further subject of the invention is, therefore, a medicament which can be administered intravenously and which contains the immunoglobulin preparations, produced in accordance with the invention, in a suitable galenical formulation. The immunoglobulins which have been treated by mild sulfitolysis and subsequently purified as described can, after the usual sterile filtration, be filled into ampoules in any desired quantity for consumption. If it is intended to use the preparation in the form of a 5 to 16% strength protein solution, a suitable formulation of the purified solution which has been sterilized by filtration can be made without difficulty. A solution which contains 0.3–0.9% of a neutral salt and to which, if desired, physiologically acceptable additives, for example an α-aminoacid, such as glycine, are also added in a concentration of 1.5–2.5%, can be freeze-dried, stored as a freeze-dried product and reconstituted in the form of a solution before use by adding the desired quantity of distilled water. This solution also exhibits no increased complement-fixation. The reconstituted agent can be administered intravenously in a similar manner.

The invention is illustrated in greater detail in the following examples:

EXAMPLE 1

The gamma-globulin fraction produced in the fractionation of albumin by Cohn's method with the aid of ethanol is dissolved in a 0.3% strength solution of sodium chloride, 10 liters of sodium chloride solution being used for 1 kg of the gamma-globulin paste. The temperature is kept at about 5° C. 0.07% (g/vol) of $Na_2S_2O_5$, in the form of a 10% strength sodium metabisulfite solution, and 0.007% (g/vol) of $CuSO_4.5H_2O$, in the form of a 1% strength copper sulfate solution, are added to the solution. After this addition has been made, 200 ml of a 0.2 molar $AlCl_3$ solution and 200 ml of a 0.2 molar $Na_3PO_4$ solution are added, per liter of the solution. The addition is made whilst controlling the pH; this control should ensure a pH value of about 5. The solution is stirred overnight at 5° C. The aluminum phosphate adsorbent is then removed by centrifuging.

The solution containing the immunoglobulins is precipitated by adding 25% (vol/vol) of ethanol. The precipitate is isolated by centrifuging. It is dissolved in a sufficient quantity of distilled water, 0.2% of ethylenediamine-tetraacetic acid is added and the pH value is adjusted to 7.0. The immunoglobulins are precipitated again by adding 25% of ethanol and are isolated by centrifuging and the precipitate is dissolved in a sufficient quantity of 0.85% strength sodium chloride solution. 2.5% (g/v) of glycine are added to this solution. The preparation is then lyophilized.

The preparation of the immunoglobulin which can be administered intravenously can be finished in the following manner: the lyophilisate is dissolved in distilled water and the solution is adjusted to a protein content of 5%, filled into the final containers and lyophilized again.

EXAMPLE 2

The gamma-globulin fraction produced in the fractionation of albumin by Cohn's method with the aid of ethanol is dissolved in a 0.3% strength solution of sodium chloride, 10 liters of sodium chloride solution being used for 1 kg of gamma-globulin paste. The temperature is kept at about 5° C. 0.2% (g/vol) of $Na_2S_2O_5$, in the form of a 10% strength sodium metabisulfite solution, is added to the solution, followed by 0.02% (g/vol) of $CuSO_4.5H_2O$, in the form of a 1% strength copper sulfate solution. After the end of the additions, 120 ml of a 1 molar calcium acetate solution and 120 ml of a ½ molar solution of secondary sodium phosphate are added, per liter of solution, whilst stirring. The pH value is kept at 8±0.1 with 0.1 M sodium hydroxide solution. The mixture is stirred for 20 hours at 5° C. At the end of this time, the calcium phosphate which has been formed is removed by filtration and the filtered immunoglobulin solution is isolated.

The immunoglobulins can be worked up further in accordance with Example 1.

What is claimed is:

1. A method for making an immunoglobulin preparation having reduced complement activity, which method comprises treating an immunoglobulin fraction with at least one member selected from the group consisting of (1) sulfitolytic agents and (2) phosphates which are sparingly soluble in water, said treatment with a sulfitolytic agent proceeding for 5 to 90 hours at a temperature not substantially higher than about 50° C. and at a concentration of said sulfitolytic agent which is less than $5(10^{-2})$ mole/liter, and said treatment with a phosphate being at a concentration of phosphate from 0.005 mole/liter to 0.15 mole/liter.

2. A method as in claim 1 wherein said immunoglobulin fraction is treated with a sulfitolytic agent.

3. A method as in claim 1 wherein said immunoglobulin fraction is treated with a phosphate.

4. A method as in claim 1 wherein said immunoglobulin fraction is treated with both a sulfitolytic agent and a phosphate.

5. A method as in claim 1 wherein said sulfitolytic agent is a sulfite or bisulfite.

6. A method as in claim 1 wherein said treatment with a sulfitolytic agent is carried out in the presence of heavy metal ions at a concentration thereof of less than $5(10^{-3})$ mole/liter.

7. A method as in claim 6 wherein said heavy metal ions are copper-II ions.

8. A method as in claim 1 wherein said immunoglobulin fraction contains 20 to 60 percent of other plasma proteins in addition to immunoglobulins.

9. A method as in claim 1 wherein an immunoglobulin fraction consisting of 40 to 80 percent of immunoglobulin and 20 to 60 percent of other plasma proteins is treated at a pH from 5 to 8, at a protein concentration of 1 to 5 percent, with from $2(10^{-3})$ mole/liter to $4(10^{-3})$ mole/liter of $Na_2S_2O_5$ and with from $2(10^{-4})$ mole/liter to $4(10^{-4})$ mole/liter of $CuSO_4$, and then said proteins are isolated.

10. A method as in claim 9 wherein the treated immunoglobulins are concentrated and purified.

11. A method as in claim 1 wherein said phosphate is prepared in situ in said immunoglobulin fraction.

12. A method as in claim 11 wherein said phosphate is aluminum phosphate.

13. A method as in claim 11 wherein said phosphate is calcium phosphate.

14. An immunoglobulin preparation made by the method of claim 1.

15. An immunoglobulin preparation made by the method of claim 2.

16. An immunoglobulin preparation made by the method of claim 3.

17. An immunoglobulin preparation made by the method of claim 4.

* * * * *